US012686115B2

(12) United States Patent
Tadano

(10) Patent No.: US 12,686,115 B2
(45) Date of Patent: Jul. 21, 2026

(54) WORK ASSISTANCE ROBOT

(71) Applicant: RIVERFIELD INC., Tokyo (JP)

(72) Inventor: Kotaro Tadano, Tokyo (JP)

(73) Assignee: RIVERFIELD INC., Tokyo (JP)

( * ) Notice: Subject to any disclaimer, the term of this patent is extended or adjusted under 35 U.S.C. 154(b) by 330 days.

(21) Appl. No.: 18/300,054

(22) Filed: Apr. 13, 2023

(65) Prior Publication Data

US 2023/0256590 A1     Aug. 17, 2023

Related U.S. Application Data

(63) Continuation of application No. PCT/JP2020/038998, filed on Oct. 15, 2020.

(51) Int. Cl.
   *B25J 9/00*       (2006.01)
   *B25J 5/00*       (2006.01)
   *B25J 15/04*      (2006.01)
   *A61B 34/30*     (2016.01)

(52) U.S. Cl.
   CPC ............. *B25J 9/0087* (2013.01); *B25J 5/007* (2013.01); *B25J 15/04* (2013.01); *A61B 34/30* (2016.02)

(58) Field of Classification Search
   CPC . B25J 9/0087; B25J 5/007; B25J 15/04; B25J 18/04; B25J 9/06; A61B 34/30; A61B 90/50
   See application file for complete search history.

(56) References Cited

U.S. PATENT DOCUMENTS

| | | | |
|---|---|---|---|
| 9,179,979 B2 | 11/2015 | Jinno | |
| 2001/0013764 A1 | 8/2001 | Blumenkranz et al. | |
| 2009/0024142 A1 | 1/2009 | Ruiz Morales | |
| 2011/0245844 A1* | 10/2011 | Jinno ..................... A61B 34/30 606/130 | |
| 2011/0262251 A1* | 10/2011 | Otogawa ........... H01L 21/67778 414/222.07 | |
| 2018/0014893 A1* | 1/2018 | Cleary ................... A61B 34/30 | |
| 2018/0185219 A1 | 7/2018 | Hashimoto | |
| 2019/0126468 A1 | 5/2019 | Haddadin et al. | |
| 2019/0216576 A1* | 7/2019 | Eyre .................. A61B 1/00149 | |
| 2020/0056738 A1* | 2/2020 | Kuzmin ................. F16B 2/065 | |
| 2020/0121403 A1 | 4/2020 | Awano et al. | |
| 2020/0360100 A1 | 11/2020 | Mantri et al. | |

FOREIGN PATENT DOCUMENTS

| | | |
|---|---|---|
| CN | 109730778 A | 5/2019 |
| CN | 110239869 A | 9/2019 |
| JP | 7-223179 A | 8/1995 |

(Continued)

OTHER PUBLICATIONS

International Search Report for PCT/JP2020/038998 dated Dec. 28, 2020.

*Primary Examiner* — Khoi H Tran
*Assistant Examiner* — Tien Minh Le
(74) *Attorney, Agent, or Firm* — Sughrue Mion, PLLC

(57) ABSTRACT

A work assistance robot includes articulated arms, lifting/lowering units that lift and lower the articulated arms, respectively, and a main housing on which the lifting/lowering units are mounted. Each articulated arm has seven or more degrees of freedom including a degree of freedom of an up-and-down movement of the lifting/lowering unit of the articulated arm.

17 Claims, 7 Drawing Sheets

(56)  References Cited

FOREIGN PATENT DOCUMENTS

| JP | 8-70033 | A | 3/1996 |
| JP | 2009-525098 | A | 7/2009 |
| JP | 2011-206312 | A | 10/2011 |
| JP | 2020-65644 | A | 4/2020 |
| WO | 2017002142 | A1 | 1/2017 |
| WO | 2020/181290 | A1 | 9/2020 |

* cited by examiner

10

10

10

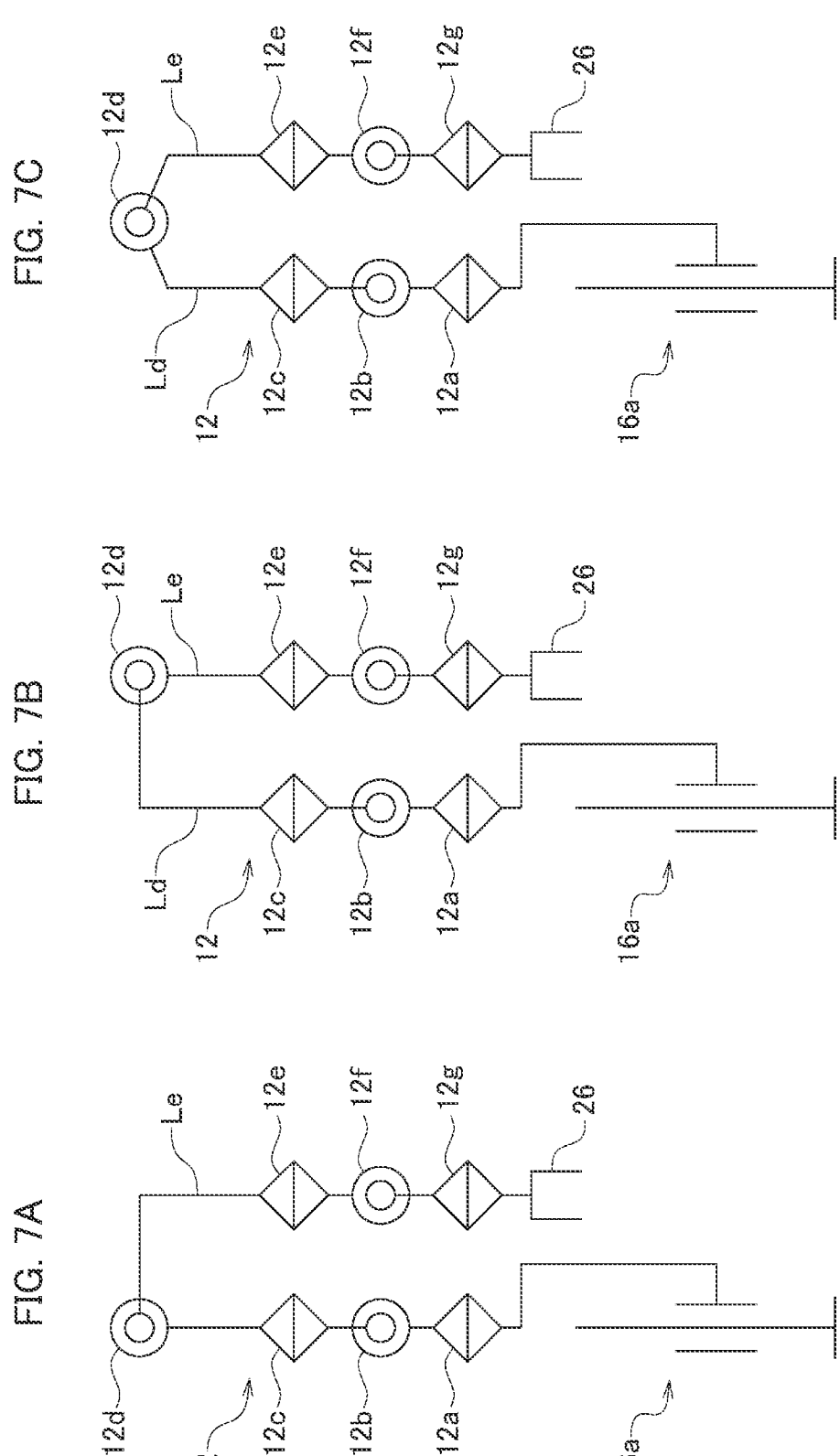

WORK ASSISTANCE ROBOT

CROSS REFERENCE TO RELATED APPLICATION

This application is a continuation application of International Patent Application No. PCT/JP2020/038998, filed on Oct. 15, 2020, the contents of which being incorporated by reference herein in its entirety.

BACKGROUND

The present disclosure relates to a work assistance robot.

Medical treatments using robots (manipulators) have recently been proposed in order to reduce the burden on operators and save manpower in medical facilities. In the field of surgery, proposals have been made for surgical manipulator systems for operators to treat patients by operating remotely-controllable surgical manipulators. A robot system performs behaviors relating to nursing care and medical care on a human.

SUMMARY

According to an aspect of one or more embodiments, there is provided a work assistance robot comprising a plurality of articulated arms; a plurality of lifting/lowering units configured to lift and lower the plurality of articulated arms, respectively; and a main unit on which the plurality of lifting/lowering units are mounted, wherein each of the plurality of articulated arms has seven or more degrees of freedom including a degree of freedom of an up-and-down movement of the lifting/lowering unit of the articulated arm.

According to another aspect of one or more embodiments, there is provided a work assistance robot comprising two articulated arms; two lifting/lowering units on which the two articulated arms are respectively mounted, the two lifting/lowering units configured to lift and lower the two articulated arms, respectively; and a housing to which the two lifting/lowering units are mounted, wherein each of the two articulated arms has seven or more degrees of freedom including a degree of freedom of an up-and-down movement of the articulated arm.

According to yet another aspect of one or more embodiments, there is provided a work assistance robot comprising a housing; a first articulated arm; a second articulated arm; a first shaft connected to the housing and to the first articulated arm and a first motor attached to the first shaft to lift and lower the first articulated arm in a vertical direction with respect to the housing; and a second shaft connected to the housing and to the second articulated arm and a second motor attached to the second shaft to lift and lower the second articulated arm in a vertical direction with respect to the housing, wherein the first articulated arm has seven or more degrees of freedom including a degree of freedom of an up-and-down movement of the first articulated arm, and the second articulated arm has seven or more degrees of freedom including a degree of freedom of an up-and-down movement of the second articulated arm, and wherein, when the first articulated arm is moved to a position higher than the second articulated arm by the first motor, the first articulated arm is extendable laterally with respect to the housing while overlapping with the second articulated arm in the vertical direction.

BRIEF DESCRIPTION OF DRAWINGS

The above and/or other aspects will become apparent and more readily appreciated from the following description of various embodiments, taken in conjunction with the accompanying drawings, in which:

FIGS. 7A-7C are schematic diagrams illustrating various states in which an articulated arm is folded at a joint, according to some embodiments.

DETAILED DESCRIPTION

Figure 1:
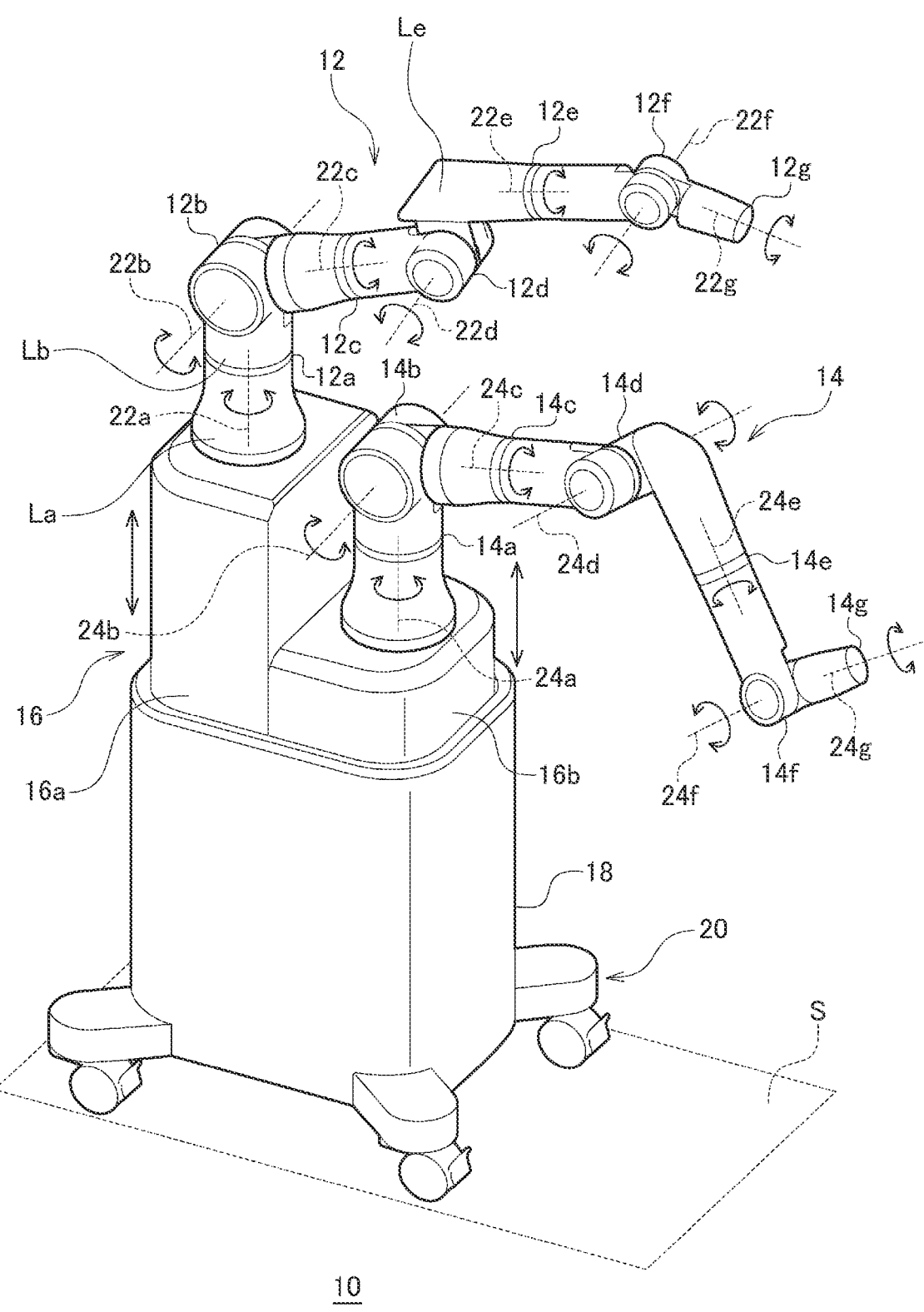
FIG. 1 is a perspective view of a work assistance robot according to some embodiments.

As discussed above, a robot system may perform behaviors relating to nursing care and medical care on a human and may do so by using a plurality of articulated (multijointed) arms mounted on a base.

In some robot systems, two articulated arms mounted on the aforementioned robot system, however, are configured to extend from the base, which is fixed under a bed, to respective sides of the bed to perform treatment on a person. Thus, during the treatment on a person by using the articulated arms, a caregiver or medical personnel needs to avoid interference with the articulated arms, and the position and the movement of a caregiver or medical personnel are therefore limited.

Various embodiments have been made in view of the aforementioned circumstances, and it is an aspect to provide a novel technology for allowing a plurality of articulated arms to perform required movements and take required postures in a space-saving manner.

A work assistance robot according to an aspect of one or more embodiments may include a plurality of articulated arms; lifting/lowering units for lifting and lowering the plurality of articulated arms, respectively; and a main unit on which the lifting/lowering units are mounted. The articulated arms each have seven or more degrees of freedom including a degree of freedom of up-and-down movements of the lifting/lowering unit.

According to this aspect, the positions of a plurality of articulated arms can be shifted in the height direction relative to each other by the lifting/lowering units, and the articulated arms can therefore be directed in the same direction without interfering with each other. This configuration allows the plurality of articulated arms to take required postures and perform required movements in a space-saving manner. Furthermore, the plurality of articulated arms can be made to approach an object of work assistance from one side of the object instead of respective sides of the object.

In some embodiments, the plurality of articulated arms may include a first articulated arm and a second articulated arm. The lifting/lowering units may include a first lifting/lowering unit for lifting and lowering the first articulated arm and a second lifting/lowering unit for lifting and lowering the second articulated atm. When the first articulated arm is moved to a position higher than the second articulated arm by the first lifting/lowering unit, the first articulated arm may be extendable toward an object of work assistance while overlapping with the second articulated arm when viewed in a vertical direction. Thus, a projected area of the first articulated arm and the second articulated arm on a horizontal plane becomes small, and the work of workers such as a caregiver or medical personnel around the work assistance robot are facilitated without interference with the articulated arms.

In some embodiments, the first articulated arm may include a first joint being closest to the first lifting/lowering unit and a second joint being next to the first joint. The first joint may have a first rotation axis that is along an axis of up-and-down movements of the first lifting/lowering unit. The second joint may have a second rotation axis that intersects with the first rotation axis. Thus, because the work assistance robot can have a structure constituted by links that extend vertically from the first lifting/lowering unit to the second joint, the area occupied by the work assistance robot can be made small.

In some embodiments, the second articulated arm may include a third joint being closest the second lifting/lowering unit and a fourth joint being next to the third joint. The third joint may have a third rotation axis that is along an axis of up-and-down movements of the second lifting/lowering unit. The fourth joint may have a fourth rotation axis that intersects with the third rotation axis. Thus, because the work assistance robot can have a structure constituted by links that extend vertically from the second lifting/lowering unit to the fourth joint, the area occupied by the work assistance robot can be made small.

In some embodiments, the first lifting/lowering unit and the second lifting/lowering unit may be arranged adjacent to each other on an upper part of the main unit. As a result, the lifting/lowering units can be prevented from sticking out laterally from the main unit, and the area occupied by the work assistance robot can therefore be made small.

In some embodiments, a moving mechanism for moving the main unit to a predetermined position relative to an object of work assistance may further be included. This configuration allows the work assistance robot to be placed at a position at which the work assistance robot does not interfere with a worker.

In some embodiments, the articulated arms may each have, at a leading end thereof, an attachment part to which one of a plurality of kinds of end effectors to be used as a surgical tool is selectively attachable.

Note that any combination of the components described above, and any expression in the present disclosure may be converted to that for a method, a device, a system, and the like and is included in the scope of the present disclosure.

According to various embodiments, a plurality of articulated arms can perform required movements and take required postures in a space-saving manner.

Various embodiments will now be described with reference to the drawings. Components, members, and processes that are the same as or equivalent to each other illustrated in the drawings are represented by the same reference numerals, and redundant explanation will not be repeated where appropriate for conciseness. The various embodiments are not to limit the present disclosure, but are only provided as examples, and any feature or any combination of features described in a given embodiment is not necessarily essential to the present disclosure.

Figure 2:
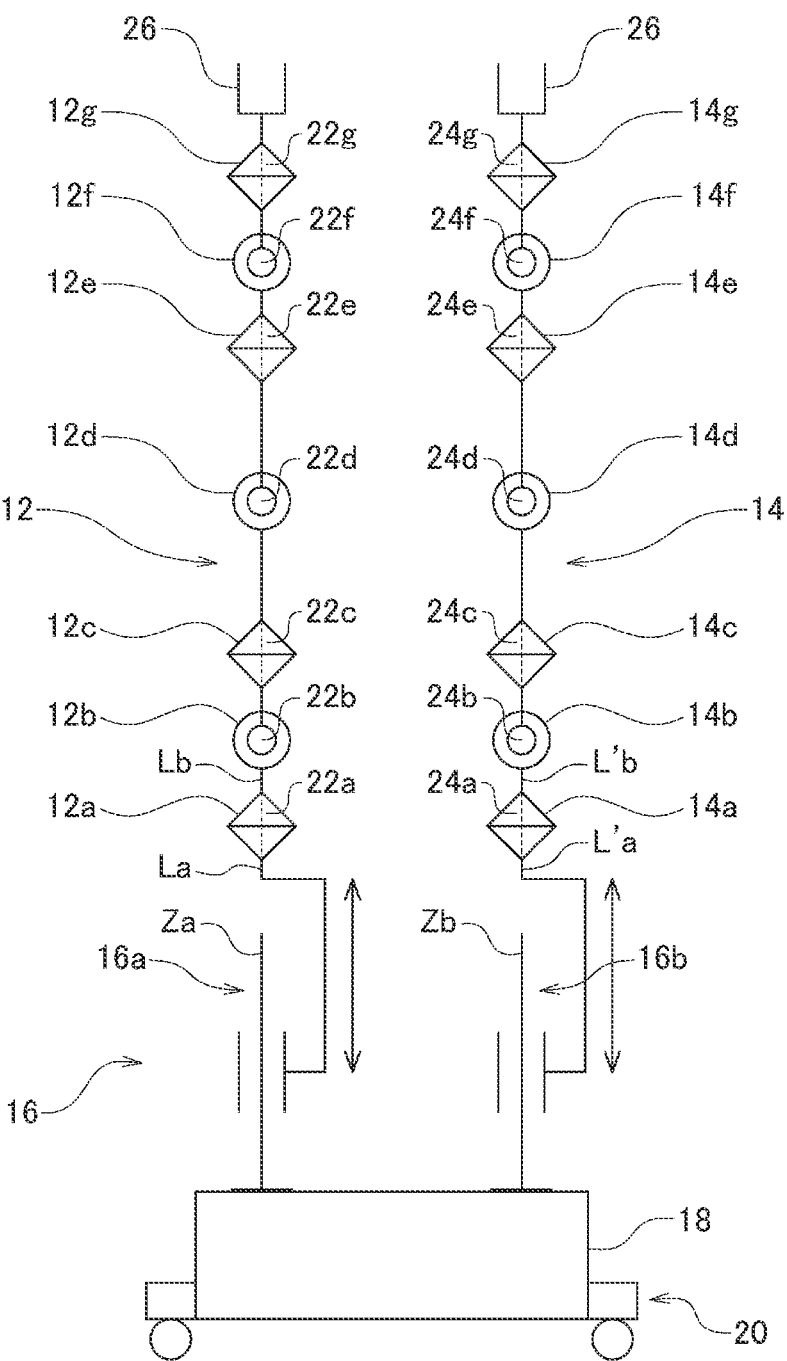
FIG. 2 is a diagram illustrating a mechanism of the work assistance robot of FIG. 1, according to some embodiments.
Figure 3:
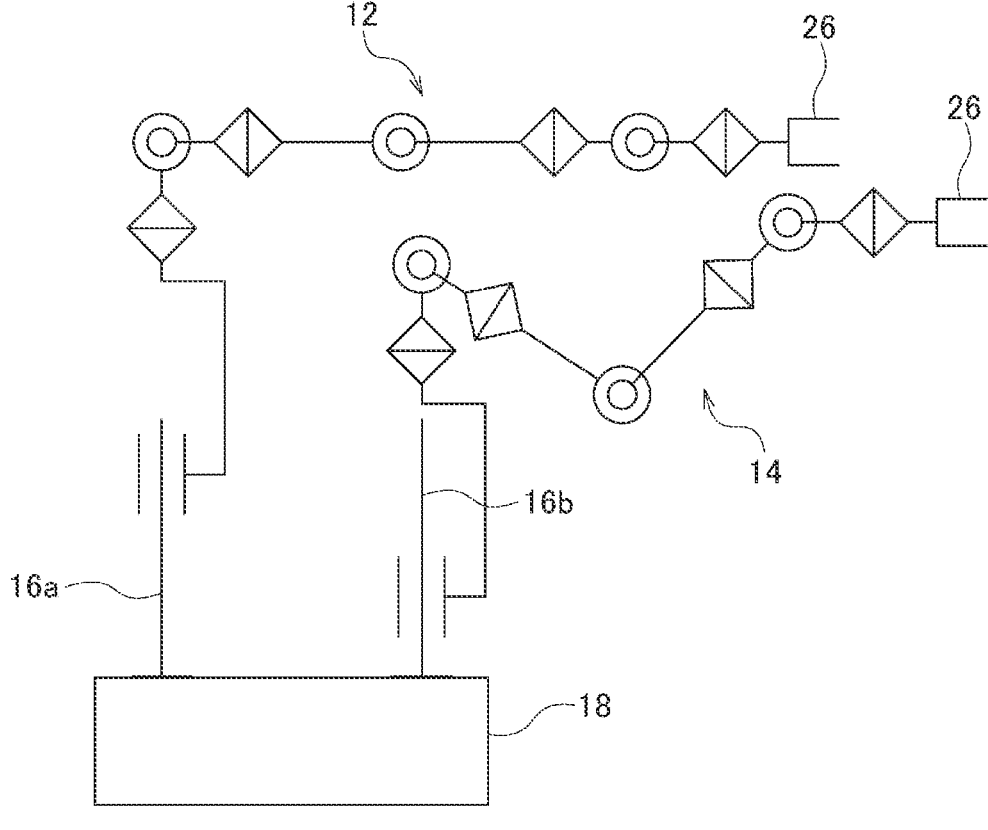
FIG. 3 is a diagram illustrating the mechanism of the work assistance robot in a state in which a plurality of articulated arms are directed in the same direction, according to some embodiments.

FIG. 1 is a perspective view of a work assistance robot according to some embodiments. FIG. 2 is a diagram illustrating a mechanism of the work assistance robot of FIG. 1, according to some embodiments. FIG. 3 is a diagram illustrating the mechanism of the work assistance robot in a state in which a plurality of articulated arms are directed in the same direction, according to some embodiments. The work assistance robot 10 illustrated in FIG. 1 includes a plurality of articulated (multi-jointed) arms 12 and 14, lifting/lowering units 16 that individually lift and lower the articulated arms 12 and 14, a main unit 18 on which the lifting/lowering units 16 are mounted, and a moving mechanism 20 for moving the main unit 18 to predetermined positions relative to an object of work assistance.

Figure 4:
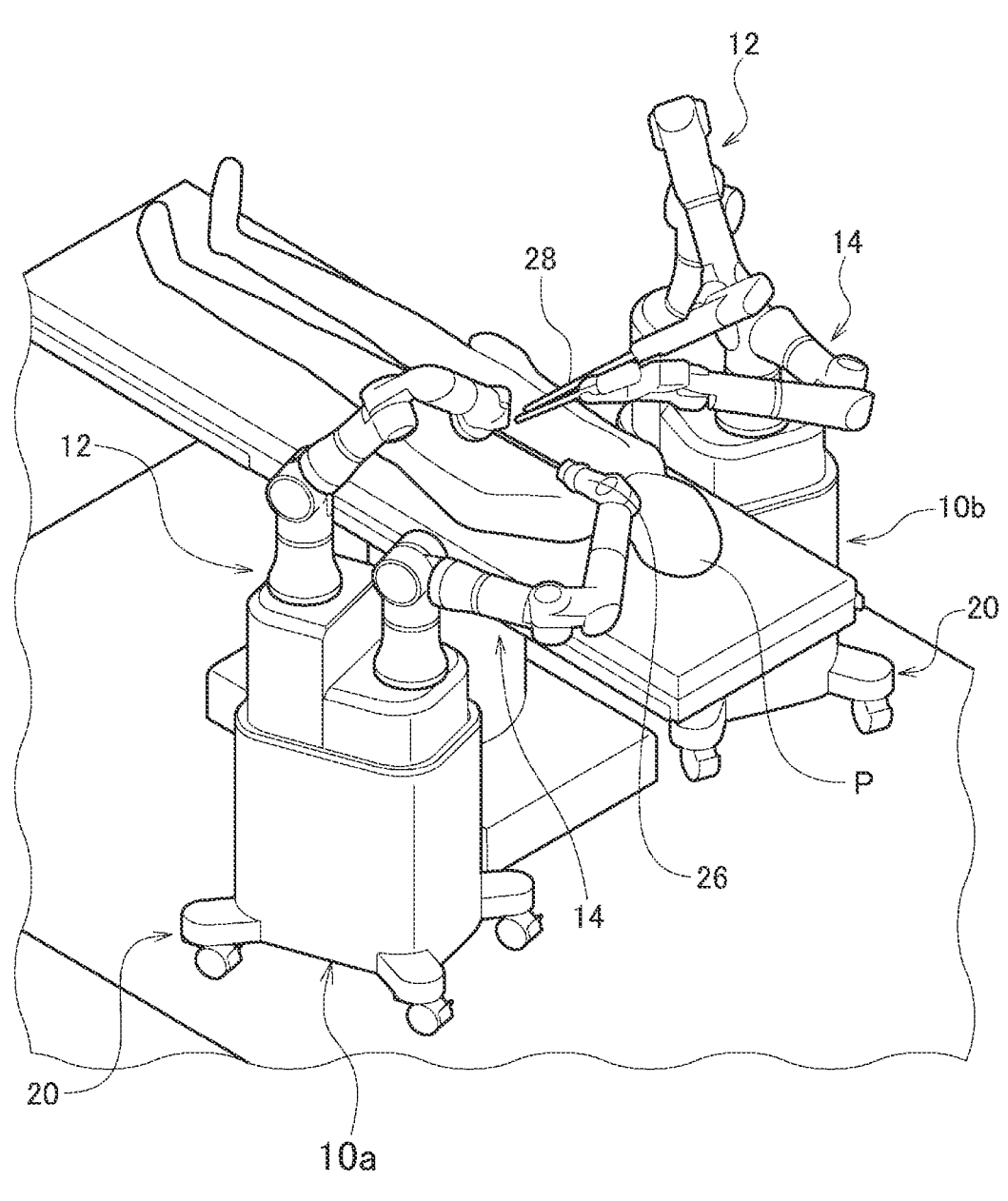
FIG. 4 is a schematic diagram illustrating a state in which a plurality of work assistance robots are used to perform an operation on a patient lying on a bed, according to some embodiments.
Figure 5:
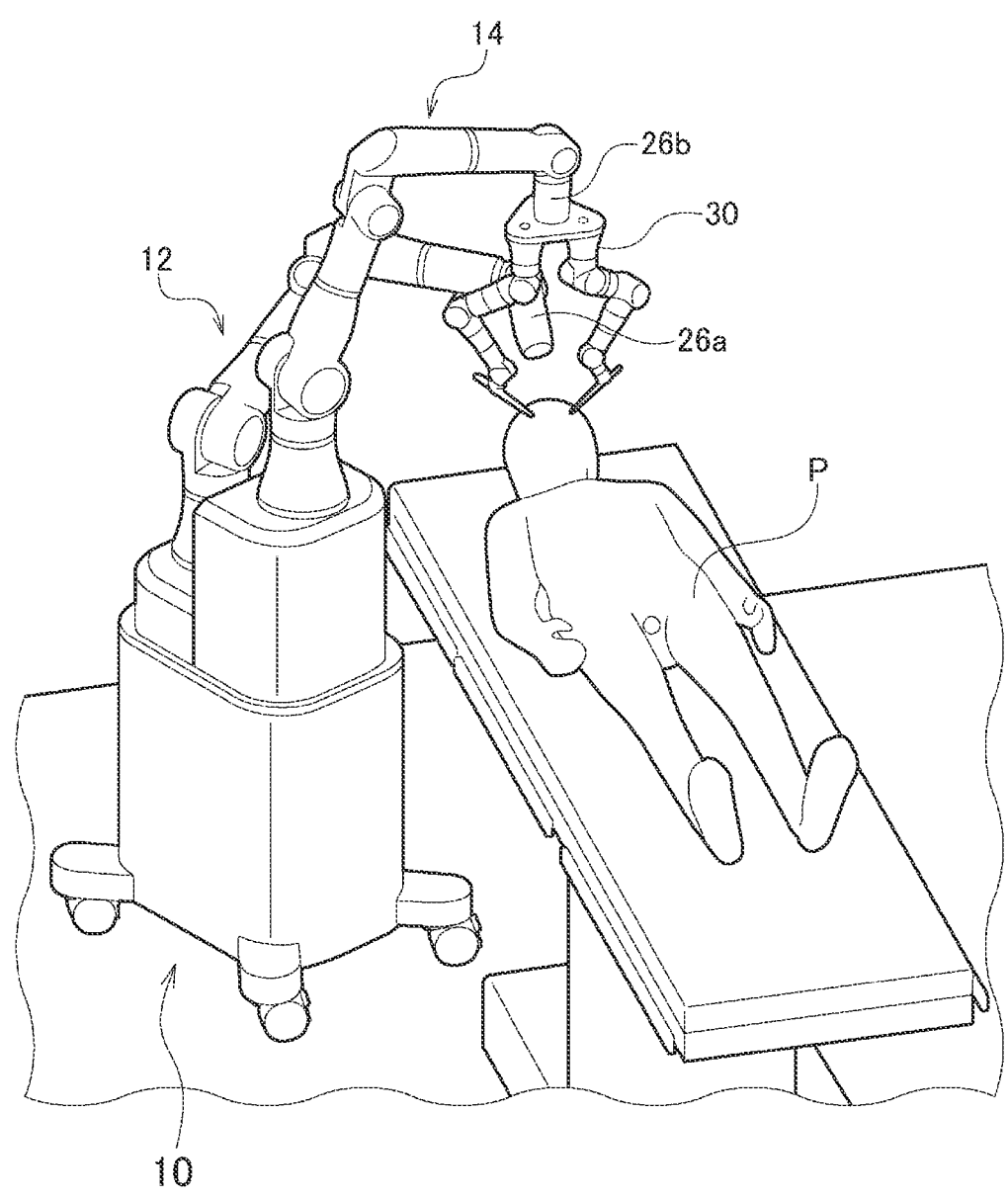
FIG. 5 is a schematic diagram illustrating a state in which a work assistance robot is used to examine a patient lying on a bed, according to some embodiments.
Figure 6:
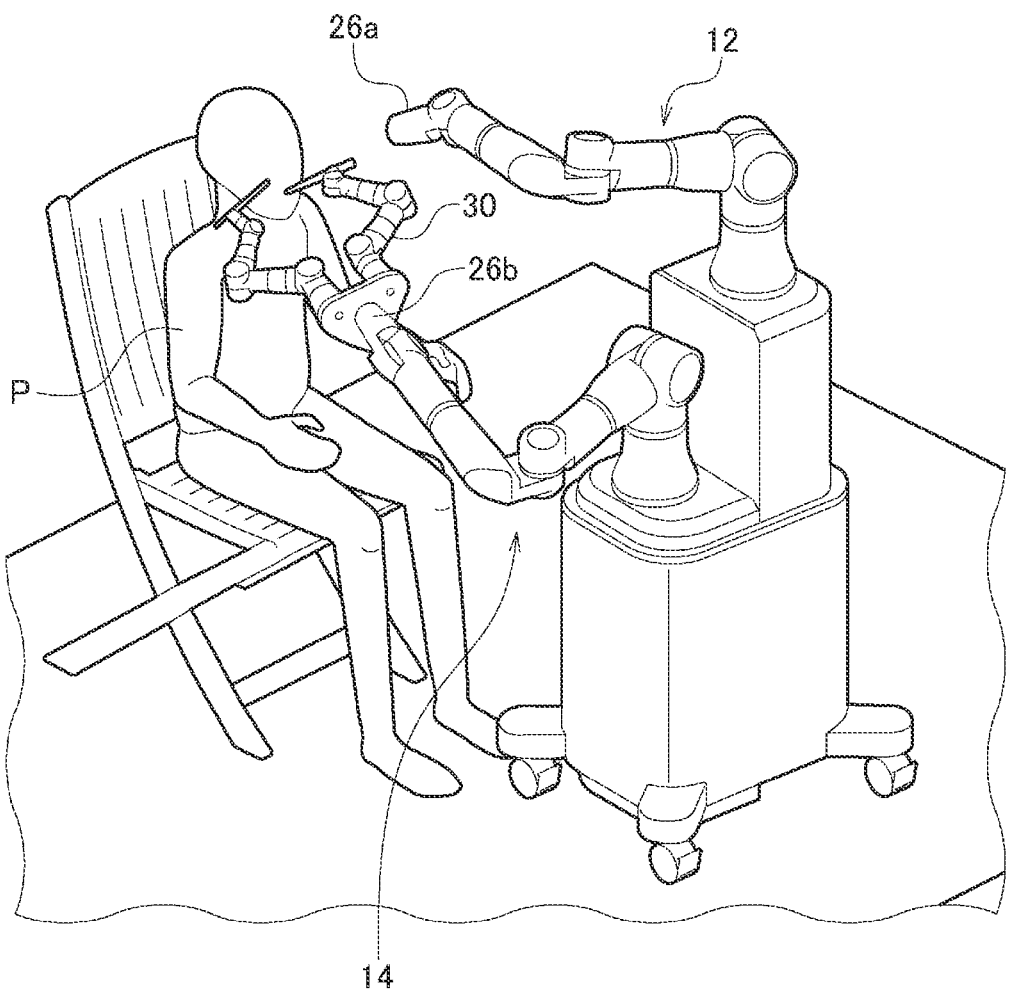
FIG. 6 is a schematic diagram illustrating a state in which a work assistance robot is used to examine a patient sitting in a chair, according to some embodiments.

In some embodiments, the main unit 18 may be, for example, a main body or housing of the work assistance robot 10. In some embodiments, the moving mechanism 20 may be, for example, a plurality of legs, each leg having a caster attached thereto. In such a configuration, the legs may be mounted to the main body or housing of the work assistance robot such that the work assistance robot 10 may be moved into various positions as illustrated in FIGS. 4-6 by way of example.

In some embodiments, each of the lifting/lowering units 16 may be, for example, a shaft and a motor attached to the shaft such that the shaft may be raised and lowered by the motor. The lifting/lowering units 16 include a first lifting/lowering unit 16a for lifting and lowering the articulated arm 12, and a second lifting/lowering unit 16b for lifting and lowering the articulated arm 14. The articulated arm 12 has seven joints 12a to 12g arranged in this order outward from the first lifting/lowering unit 16a. The articulated arm 14 has seven joints 14a to 14g arranged in this order outward from the second lifting/lowering unit 16b.

The joints 12a to 12g have rotation axes 22a to 22g, respectively, and the joints 14a to 14g have rotation axes 24a to 24g, respectively. The articulated arm 12 thus has eight degrees of freedom (seven or more degrees of freedom) including up-and-down movement caused by the first lifting/lowering unit 16a. Similarly, the articulated arm 14 has eight degrees of freedom (seven or more degrees of freedom including up-and-down movements caused by the second lifting/lowering unit 16b.

Because the work assistance robot 10 according to some embodiments can shift the positions of a plurality of articulated arms 12 and 14 in the height direction relative to each other by using the lifting/lowering units 16 as illustrated in FIGS. 1 and 3, the articulated arms 12 and 14 can be directed in the same direction without interfering with each other. This configuration allows a plurality of articulated arms 12 and 14 to take required postures and perform required movements in a space-saving manner.

In addition, as illustrated in FIGS. 1 and 3, the articulated arm 12, which has been moved by the first lifting/lowering unit 16a to a position higher than the articulated arm 14, can extend toward the object of work assistance while overlapping with the articulated arm 14 when viewed in the vertical direction. Thus, as illustrated in FIG. 1, a projected area S of the articulated arm 12 and the articulated arm 14 on a horizontal plane becomes small, and work of workers such as a caregiver or medical personnel around the work assistance robot 10 are facilitated without interference with the articulated arms 12 and 14.

In some embodiments, the first lifting/lowering unit 16*a* and the second lifting/lowering unit 16*b* may be arranged adjacent to each other on an upper part of the main unit 18 of the work assistance robot 10. This configuration prevents the lifting/lowering units 16 from sticking out laterally from the main unit 18, and therefore reduces the area occupied by the work assistance robot 10.

The articulated arm 12 includes the joint 12*a*, which is the closest to the first lifting/lowering unit 16*a*, and the joint 12*b* next to the joint 12*a*. The joint 12*a* has the rotation axis 22*a* along an axis Za of up-and-down movements of the first lifting/lowering unit 16*a*. Note that the rotation axis 22*a* along the axis Za is not limited to a case where the rotation axis 22*a* is parallel to the axis Za but may include cases where the angle between the axis Za and the rotation axis 22*a* is in a range of, for example, 0±45°, a range of 0±30°, or a range of 0±15° according to various embodiments.

The joint 12*b* has the rotation axis 22*b* that intersects with the rotation axis 22*a*. Note that the rotation axis 22*b* that intersects with the rotation axis 22*a* is not limited to a case where the rotation axis 22*a* and the rotation axis 22*b* are at right angles to each other but may include cases where the angle between the rotation axis 22*a* and the rotation axis 22*b* is in a range of, for example, 90±45°, a range of 90±30°, or a range of 90±15° according to various embodiments. Thus, because the work assistance robot 10 can have a structure constituted by links La and Lb that extend vertically from the first lifting/lowering unit 16*a* to the joint 12*b*, the joint 12*b* and the links La and Lb do not project out laterally from the main unit 18, and the area occupied by the work assistance robot 10 can be made small.

The articulated arm 14 includes the joint 14*a*, which is the closest to the second lifting/lowering unit 16*b*, and the joint 14*b* next to the joint 14*a*. The joint 14*a* has the rotation axis 24*a* along an axis Zb of up-and-down movements of the second lifting/lowering unit 16*b*. Note that the rotation axis 24*a* along the axis Zb is not limited to a case where the rotation axis 24*a* is parallel to the axis Zb but may include cases where the angle between the axis Zb and the rotation axis 24*a* is in a range of 0±45°, a range of, for example, 0±30°, or a range of 0±15° according to various embodiments.

The joint 14*b* has the rotation axis 24*b* that intersects with the rotation axis 24*a*. Note that the rotation axis 24*b* that intersects with the rotation axis 24*a* is not limited to a case where the rotation axis 24*a* and the rotation axis 24*b* are at right angles to each other but may include cases where the angle between the rotation axis 24*a* and the rotation axis 24*b* is in a range of, for example, 90±45°, a range of 90±30°, or a range of 90±15° according to various embodiments. Thus, because the work assistance robot 10 can have a structure constituted by links L'a and L'b that extend vertically from the second lifting/lowering unit 16*b* to the joint 14*b*, the joint 14*b* and the links L'a and L'b do not stick out laterally from the main unit 18, and the area occupied by the work assistance robot 10 can be made small.

In some embodiments, the work assistance robot 10 may be configured such that one of the articulated arm 12 and the articulated arm 14 that is at a position higher than the other can move 360° around the main unit 18. As a result, a working space in which the articulated arms can be positioned to reach desired regions increases, and it becomes easier to place the work assistance robot 10 at a position where the work assistance robot 10 is less likely to interfere with a worker.

The articulated arms 12 and 14 each have, at a leading end thereof, an attachment part 26 to which one of a plurality of kinds of end effectors to be used as a surgical tool can be selectively attached. Examples of end effectors to be used as a surgical tool include, for example, a forceps device, an endoscope, and the like.

Next, some use states of the work assistance robot 10 will be explained. FIG. 4 is a schematic diagram illustrating a state in which a plurality of work assistance robots are used to perform an operation on a patient lying on a bed, according to some embodiments. FIG. 5 is a schematic diagram illustrating a state in which a work assistance robot is used to examine a patient lying on a bed, according to some embodiments. FIG. 6 is a schematic diagram illustrating a state in which a work assistance robot is used to examine a patient sitting in a chair, according to some embodiments.

As illustrated in FIG. 4, in some embodiments, a plurality of work assistance robots may be provided. Each of work assistance robots 10*a* and 10*b* can make a plurality of articulated arms 12 and 14 approach a patient P, which is an object of work assistance, from one side of the patient P instead of respective sides of the patient P. The work assistance robots 10*a* and 10*b* may be configured to obtain relative positions of each other on the basis of various kinds of information such as position information via radio communication, position information from a global positioning system (GPS), position information of surroundings obtained by radar, and image data obtained by imaging means such as a camera. In other words, each of the work assistance robots 10*a* and 10*b* may be provided with a memory, a microprocessor, a microcontrollers or hardware logic, a communications interface, and one or more sensors such as a GPS sensor, a radar, or a camera. With such a configuration, the microprocessor, microcontroller or hardware logic of the work assistance robot 10*a* may receive data from the one or more sensors, and control the communication interface to transmit the data to the work assistance robot 10*b*, such that the work assistance robot 10*b* may receive the data and know the state of the work assistance robot 10*a*, and vice versa.

As a result, the work assistance robots 10*a* and 10*b* can be placed at suitable positions relative to the patient P without interfering with each other. Furthermore, the work assistance robots 10*a* and 10*b* can be placed at positions that do not interfere with a doctor or a worker. In the example illustrated in FIG. 4, a forceps device 28 or an endoscope is attached to the attachment part 26 of each articulated arm.

As illustrated in FIGS. 5 and 6, the attachment part 26*a* of the articulated arm 12 may include a built-in camera for imaging an affected part of the patient P or a treatment part. In some embodiments, a treatment tool 30 for examining the patient P may be attached to the attachment part 26*b* of another articulated arm 14.

[Folding Arm]

FIGS. 7A-7C are schematic diagrams illustrating various states in which an articulated arm is folded at a joint, according to some embodiments.

At the articulated arm 12 illustrated in FIG. 7A, a link Le connecting the joint 12*d* with the joint 12*e* has an L shape (see FIG. 1). Thus, when the articulated arm 12 is folded at the joint 12*d*, the links from the joint 12*a* to the joint 12*d* and the links from the joint 12*e* to the joint 12*g* can be made substantially parallel to each other.

At the articulated arm 12 illustrated in FIG. 7B, a link Ld connecting the joint 12*c* with the joint 12*d* has an L shape. Thus, when the articulated arm 12 is folded at the joint 12*d*, the links from the joint 12*a* to the joint 12*c* and the links from the joint 12*d* to the joint 12*g* can be made substantially parallel to each other.

At the articulated arm 12 illustrated in FIG. 7C, a link Ld connecting the joint 12*c* and the joint 12*d* and a link Le connecting the joint 12*d* with the joint 12*e* both have a U shape (V shape). Thus, when the articulated arm 12 is folded at the joint 12*d*, the links from the joint 12*a* to the joint 12*d* and the links from the joint 12*d* to the joint 12*g* can be made substantially parallel to each other.

While various embodiments have been described above with reference to the drawings, the present disclosure is not limited to the embodiments, and any combination or substitution of components in various embodiments as appropriate is included in scope of the present disclosure. In addition, modifications such as combinations, changes in the order of processes, and various changes in design in the various embodiments may be made on the basis of knowledge of a person skilled in the art, and such modified embodiments are within the scope of the present disclosure.

Embodiments consistent with the present disclosure can be used for work assistance robots for operations, nursing care, manufacture, transportation, and so on.

It should be understood that embodiments are not limited to the various embodiments described above, but various other changes and modifications may be made therein without departing from the spirit and scope thereof as set forth in appended claims.

What is claimed is:

1. A work assistance robot comprising:
a plurality of articulated arms;
a plurality of lifting/lowering units configured to lift and lower the plurality of articulated arms, respectively; and
a main unit on which the plurality of lifting/lowering units are mounted,
wherein each of the plurality of articulated arms has seven or more degrees of freedom including a degree of freedom of an up-and-down movement of the lifting/lowering unit of the articulated arm,
the plurality of lifting/lowering units are arranged adjacent to each other on a top surface of the main unit, and
a closest joint of each of the plurality of articulated arms to the respective lifting/lowering unit extends vertically from a top surface of the respective lifting/lowering unit such that a rotation axis of the closet joint is along an axis of up-and-down movement of the respective lifting/lowering unit.

2. The work assistance robot according to claim 1, wherein:
the plurality of articulated arms include a first articulated arm and a second articulated arm,
the plurality of lifting/lowering units include a first lifting/lowering unit configured to lift and lower the first articulated arm and a second lifting/lowering unit configured to lift and lower the second articulated arm, and
when the first articulated arm is moved to a position higher than the second articulated arm by the first lifting/lowering unit, the first articulated arm is extendable toward an object of work assistance while overlapping with the second articulated arm in a vertical direction.

3. The work assistance robot according to claim 2, wherein:
the first articulated arm includes a first joint being the closest joint to the first lifting/lowering unit and a second joint being next to the first joint, the first joint has a first rotation axis that is along an axis of up-and-down movement of the first lifting/lowering unit, and
the second joint has a second rotation axis that intersects with the first rotation axis.

4. The work assistance robot according to claim 3, wherein:
the second articulated arm includes a third joint being the closest joint to the second lifting/lowering unit and a fourth joint being next to the third joint,
the third joint has a third rotation axis that is along an axis of up-and-down movement of the second lifting/lowering unit, and
the fourth joint has a fourth rotation axis that intersects with the third rotation axis.

5. The work assistance robot according to claim 1, further comprising a moving mechanism configured to move the main unit to a predetermined position relative to an object of work assistance.

6. The work assistance robot according to claim 5, wherein the moving mechanism comprises a plurality of legs and a plurality of casters mounted respectively to the plurality of legs.

7. The work assistance robot according to claim 1, wherein each of the plurality of articulated arms has, at a leading end thereof, an attachment part to which one of a plurality of kinds of end effectors used as a surgical tool is selectively attachable.

8. The work assistance robot according to claim 1, wherein each of the plurality of lifting/lowering units comprises a shaft and a motor connected to the shaft to raise and lower the shaft.

9. A work assistance robot comprising:
two articulated arms;
two lifting/lowering units on which the two articulated arms are respectively mounted, the two lifting/lowering units configured to lift and lower the two articulated arms, respectively; and
a housing to which the two lifting/lowering units are mounted,
wherein each of the two articulated arms has seven or more degrees of freedom including a degree of freedom of an up-and-down movement of the articulated arm,
wherein each articulated arm is mounted to the respective lifting/lowering unit via a link that extends from the lifting/lowering unit in a vertical direction, and
wherein when one articulated arm of the two articulated arms is at a position higher than the other arm of the two articulated arms, the one articulated arm is configured to rotate 360 degrees around the housing.

10. The work assistance robot according to claim 9, wherein:
the two articulated arms include a first articulated arm and a second articulated arm,
the two lifting/lowering units include a first lifting/lowering unit configured to lift and lower the first articulated arm and a second lifting/lowering unit configured to lift and lower the second articulated arm, and
when the first articulated arm is moved to a position higher than the second articulated arm by the first lifting/lowering unit, the first articulated arm is extendable toward an object of work assistance while overlapping with the second articulated arm in the vertical direction.

11. The work assistance robot according to claim 10, wherein:

the first articulated arm includes a first joint being closest to the first lifting/lowering unit and a second joint being immediately adjacent to the first joint, the first joint has a first rotation axis that is along an axis of up-and-down movement of the first lifting/lowering unit, and the second joint has a second rotation axis that intersects with the first rotation axis.

12. The work assistance robot according to claim 11, wherein:

the second articulated arm includes a third joint being closest the second lifting/lowering unit and a fourth joint being immediately adjacent to the third joint, the third joint has a third rotation axis that is along an axis of up-and-down movement of the second lifting/lowering unit, and the fourth joint has a fourth rotation axis that intersects with the third rotation axis.

13. The work assistance robot according to claim 9, wherein the two lifting/lowering units are adjacent to each other on an upper part of the housing.

14. The work assistance robot according to claim 13, further comprising a plurality of legs mounted to the housing and a plurality of casters mounted to respective ones of the plurality of legs.

15. The work assistance robot according to claim 9, further comprising a plurality of legs mounted to the housing and a plurality of casters mounted to respective ones of the plurality of legs.

16. The work assistance robot according to claim 9, wherein each of the two articulated arms has, at a distal end thereof, an attachment part to which a surgical tool is selectively attachable.

17. A work assistance robot comprising:

a housing;

a first articulated arm;

a second articulated arm;

a first shaft connected to the housing and to the first articulated arm and a first motor attached to the first shaft to lift and lower the first shaft so as to lift and lower the first articulated arm in a vertical direction with respect to the housing; and a second shaft connected to the housing and to the second articulated arm and a second motor attached to the second shaft to lift and lower the second shaft so as to lift and lower the second articulated arm in a vertical direction with respect to the housing, wherein the first articulated arm has seven or more degrees of freedom including a degree of freedom of an up-and-down movement of the first articulated arm, and the second articulated arm has seven or more degrees of freedom including a degree of freedom of an up-and-down movement of the second articulated arm, and wherein, when the first articulated arm is moved to a position higher than the second articulated arm by the first motor, the first articulated arm is extendable laterally with respect to the housing while overlapping with the second shaft in the vertical direction.

* * * * *